(12) United States Patent
Pietruske et al.

(10) Patent No.: US 7,795,883 B2
(45) Date of Patent: Sep. 14, 2010

(54) GRID SENSOR

(75) Inventors: Heiko Pietruske, Pirna (DE); Tobias Suehnel, Dresden (DE); Horst-Michael Prasser, Daettwil (CH)

(73) Assignee: Forschungszentrum Dresden - Rossendorf E.V., Dresden (DE)

(*) Notice: Subject to any disclaimer, the term of this patent is extended or adjusted under 35 U.S.C. 154(b) by 168 days.

(21) Appl. No.: 11/919,736

(22) PCT Filed: Apr. 15, 2006

(86) PCT No.: PCT/DE2006/000671

§ 371 (c)(1),
(2), (4) Date: Oct. 30, 2007

(87) PCT Pub. No.: WO2006/114081

PCT Pub. Date: Nov. 2, 2006

(65) Prior Publication Data

US 2008/0278184 A1 Nov. 13, 2008

(30) Foreign Application Priority Data

Apr. 28, 2005 (DE) ........................ 10 2005 019 739

(51) Int. Cl.
*G01R 27/08* (2006.01)
(52) U.S. Cl. ........................ 324/722; 324/453
(58) Field of Classification Search ................. 324/733, 324/600, 453, 722
See application file for complete search history.

(56) References Cited

U.S. PATENT DOCUMENTS

| 4,404,516 A | 9/1983 | Johnson, Jr. |
| 4,644,263 A | 2/1987 | Johnson |
| 5,081,422 A | 1/1992 | Shih |
| 5,210,499 A | 5/1993 | Walsh |
| 6,314,373 B1 | 11/2001 | Prasser et al. |

FOREIGN PATENT DOCUMENTS

| DE | 282 376 | 9/1990 |
| DE | 196 49 011 | 5/1998 |

OTHER PUBLICATIONS

W. Wangjiraniran, et al., "A study of non-symmetric air water flow using wire mesh sensor"; Experimental Thermal and Fluid Science, Elsevier Science Inc., New York, US, Bd. 29, No. 3, Mar. 2005.
Horst-Michael Prasser, et al., "Evolution of the two-phase flow in a vertical tube-decomposition of gas fraction profiles according to bubble size classes using wire-mesh sensors"; International Journal of Thermal Sciences, Editions Elsevier, Paris, France, Bd. 41, No. 1. Jan. 2002.
Horst-Michael Prasser, et al., "A new electrode-mesh tomograph for gas-liquid flows"; Flow Measurement and Instrumentation, Bd. 9, 1998, pp. 111-119.

*Primary Examiner*—Vincent Q Nguyen
(74) *Attorney, Agent, or Firm*—Jordan and Hamburg LLP

(57) ABSTRACT

A grid sensor including grids of electrode wires for measuring the electroconductivity of flow medium in the cross-section of a pipeline is particularly suitable for applications where the flow medium flows at high pressure and high temperatures. Each of the electrode wires is connected to a spring via an insulating bead, the spring being arranged in a hole in a sensor body of the sensor having an axis which is oriented in a tensioning direction of the electrode wire, and fixed to the sensor body. Each of the electrode wires on the side opposing the spring is covered with an insulating tube arranged in an outwardly guided channel in the sensor body. The insulating tube ends inside the channel, in a cavity filled with a sealing material. Neither the insulating bead nor the insulating tube are located in the cross-section wherein the measurement is to be carried out.

7 Claims, 4 Drawing Sheets

GRID SENSOR

BACKGROUND OF THE INVENTION

The invention relates to a grid sensor with wire electrodes for measuring the electroconductivity of a flow medium in the cross-section of a pipeline. The invention is used in particular when the flow medium flows under high pressure and at high temperatures.

Johnson [U.S. Pat. No. 4,644,263] first describes a grid sensor that comprises electrically conducting metal wires that are under tension in the conduit cross-section and are electrically insulated from the conduit wall. Two planes of such electrode grids are installed in the conduit immediately behind one another such that the individual wires intersect at an angle of 90 degrees without touching one another. The wires are connected to an electronic circuit that connects the electrodes of the first plane via a multiplexer successively to a voltage source and then switches the electrodes of the second plane via a second multiplexer to a voltage-sensitive detector. The voltages that occur on the electrodes of the second plane are compared to a threshold value. If the latter is exceeded, it is assumed that a conductive medium, e.g. liquid, is currently at the corresponding point of intersection for the electrodes of both planes. Using the multiplexer, all available points of intersection are queried and the number of those at which the conductive phase is detected is determined. A measure for the mean volumetric portion of the conductive phase in the flow cross-section is obtained with respect to the total number of points of intersection. No information is provided about attaching or passing the electrodes through any conduit walls.

DD 282 376 A7 describes a conductive measuring cell with two electrode planes in which one plane comprises lamella-like plates arranged in the direction of flow that have slit-shaped apertures distributed uniformly across the length. A wire plane is arranged rotated by 90°. The flow is laminarized due to the lamellae added in the direction of flow and is thus heavily influenced. This patent does not provided detailed structural configuration and employment limits.

Patent DE 196 49 011 A1 describes grid sensors that comprise a circuit board, and a grid plane is soldered to each of its sides. Moreover, this patent describes a grid sensor that possesses bars with a lens-shaped cross-section rather than electrode wires. This shape of the electrodes is intended to offer greater resistivity to mechanical stresses and is thus intended for industrial use, however at the same time it is meant to assure the least possible effect on the flow and the lowest possible loss in pressure. However, it is disadvantageous that the effect on the flow is significantly higher when the bars are used than with sensors having wire electrodes. No detailed information regarding the mechanical configuration of the sensor is provided.

It is a disadvantage of the known arrangements of sensors with wire electrodes that they are not suitable for use at high pressures and high temperatures. In addition, exchanging the electrodes is difficult or even in some cases not possible for most of the known arrangements.

SUMMARY OF THE INVENTION

The object of the invention is to suggest a grid sensor that is also suitable for use as a sensor at high and changing temperatures and pressures.

The object can be attained because of the compression-resistant configuration of the basic sensor body in conjunction with new production technologies and the use of wires for measuring electrodes and the special arrangement of tensioning, insulation, and mounting elements.

The invention is described in greater detail in the following, first in general and then using two exemplary embodiments.

DETAILED DESCRIPTION OF THE INVENTION

Figure 1:
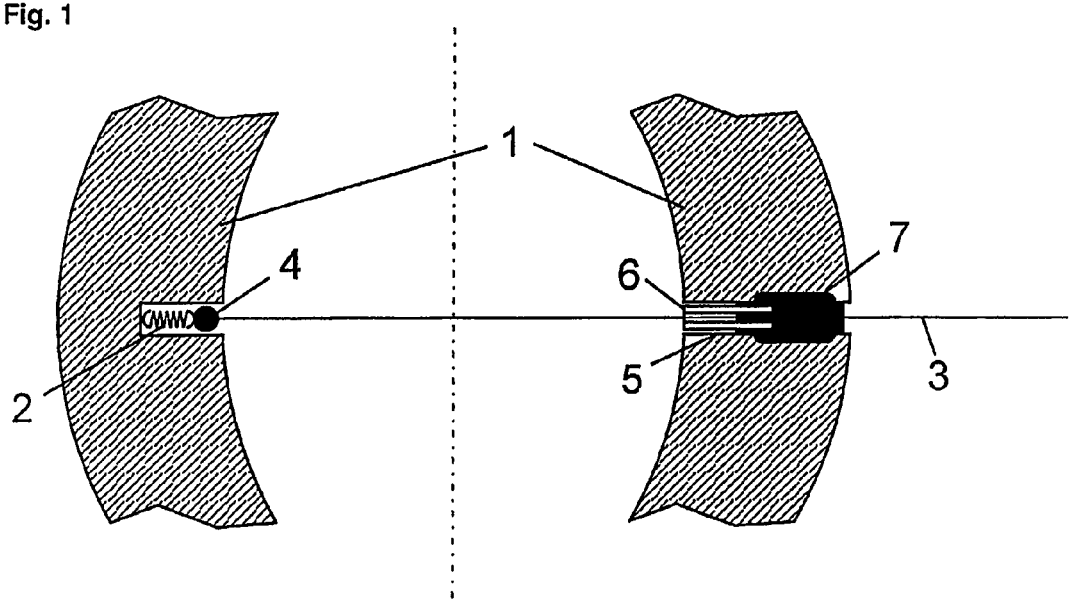
FIG. 1 depicts an electrode in cross-section.

FIG. 1 depicts an electrode in the measuring cross-section of the liquid gas flow. Each individual electrode, embodied as wire (3), is placed under tension by means of a spring (2). As can be seen in FIG. 1, the spring (2) is fixed inside of a channel that runs in the direction of tension of the wire in the sensor body (1) inside the pressure-conducting area of the sensor body (1). Moreover, each individual wire (3) is electrically insulated relative to its spring (2) by an insulating bead (4). The wires attached in this manner run through the measuring cross-section and are each conducted out of the sensor through a dedicated channel (5) to the connection site for the signal cables that connect the sensor to the data acquisition unit. Since the wires must be insulated in the channels (5) with respect the sensor body (1) as well, they are conducted in insulating tubes (6).

Figure 2:
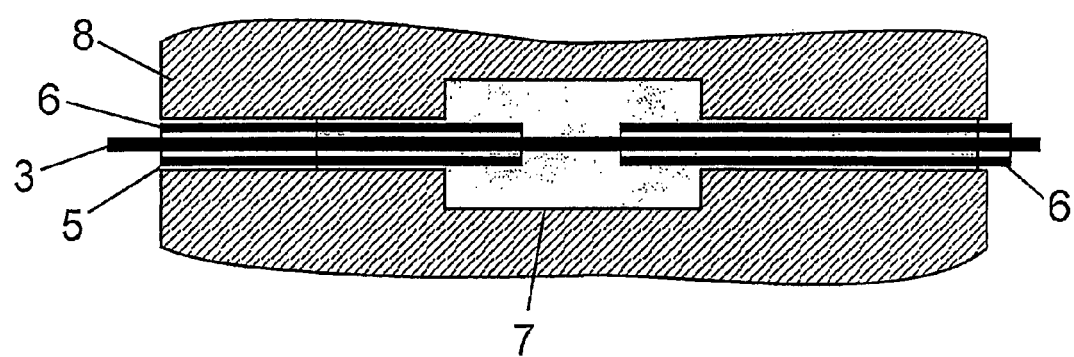
FIG. 2 depicts the seal of the channels for the electrode.

The channels (5) are sealed inside of cavities (7) by means of temperature-resistant adhesive as shown in FIG. 2. The insulating tubes (6) terminate inside the cavities (7) so that the ends of the former can be sealingly enclosed by adhesive. Across the distance from the cavities (7) to the interior wall of the sensor body (8) a temperature difference occurs that is to be designed such that even when the temperature of the measuring medium is greater than the maximum temperature of the adhesive, the temperature at the adhesive location does not exceed the maximum temperature of the adhesive. Likewise, cooling is to be provided for the sensor body in the region of the cavities (7). The insulating bead (4) and the insulating tube (6) must be produced from a material that can withstand the temperature of the measuring medium.

Figure 3:
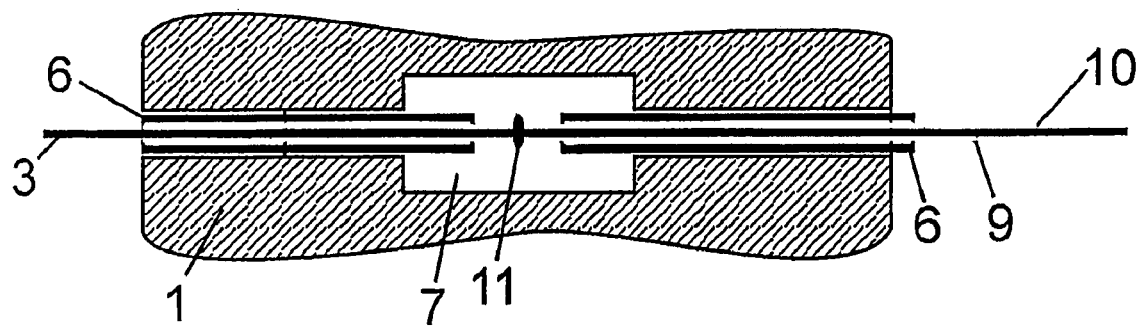
FIG. 3 depicts the electrode inside an insulating tube.

One advantageous embodiment of this arrangement of the measuring wires is depicted in FIG. 3 and is comprised in guiding the electrode wire (3) within the insulating tube (6) in a metal cannula (9) that is located in the channel (5). The cannula is guided through the cavity (7) to the outside, while the insulating tube terminates in the cavity (7). At the end of the metal cannula (9), the electrode wire (3) is sealingly soldered, welded or joined to the cannula in some other pressure-tight (10) manner. This arrangement has the advantage that the electrode wire (3) can be exchanged when damaged. In order to prevent the metal cannula (9) from shifting inside the cavity (7) filled with adhesive, an additional retention option, e.g. in the form of a soldering point (11), can be added to the cannula (9).

It is furthermore advantageous to connect the spring (2) to the sensor body (1) with a detachable connection in order to ensure that an exchange can be made there, as well.

The structural configuration of the invention is explained in greater detail using the following two examples.

Figure 4:
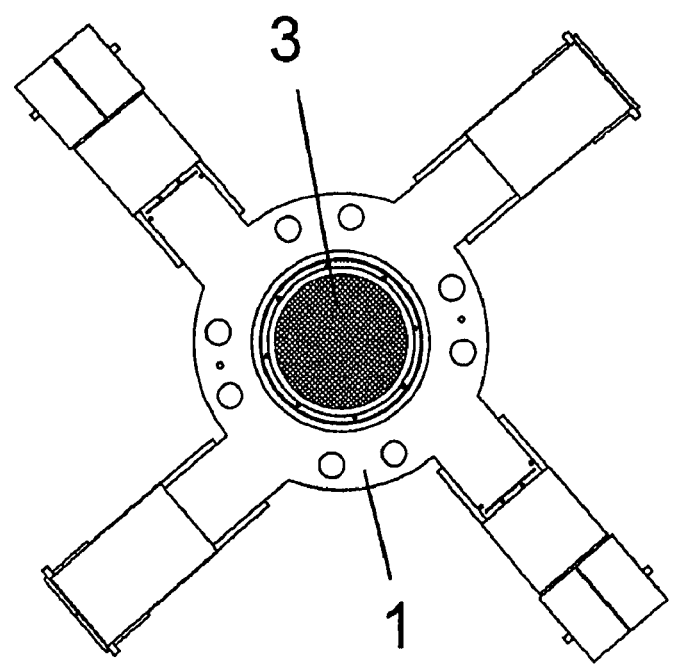
FIG. 4 depicts a grid sensor with tensile spring in a specific mount.

Example 1, which is depicted in FIG. 4, is a grid sensor as it is used for measuring conductivity in a liquid gas flow. The sensor has 2 electrode planes that are rotated 90° relative to one another and each comprises 64 electrodes. The measuring cross-section has a diameter of approx. 200 mm, which is equal to the interior diameter of the attached conduit. Thus there are 3260 measuring points in the measuring cross-section. The sensor body (1) and the electrode wires (3) comprise high-quality steel, because the sensor for measurements is employed in a steam/water mixture at up to 7 MPa and 286° C.

Figure 5:
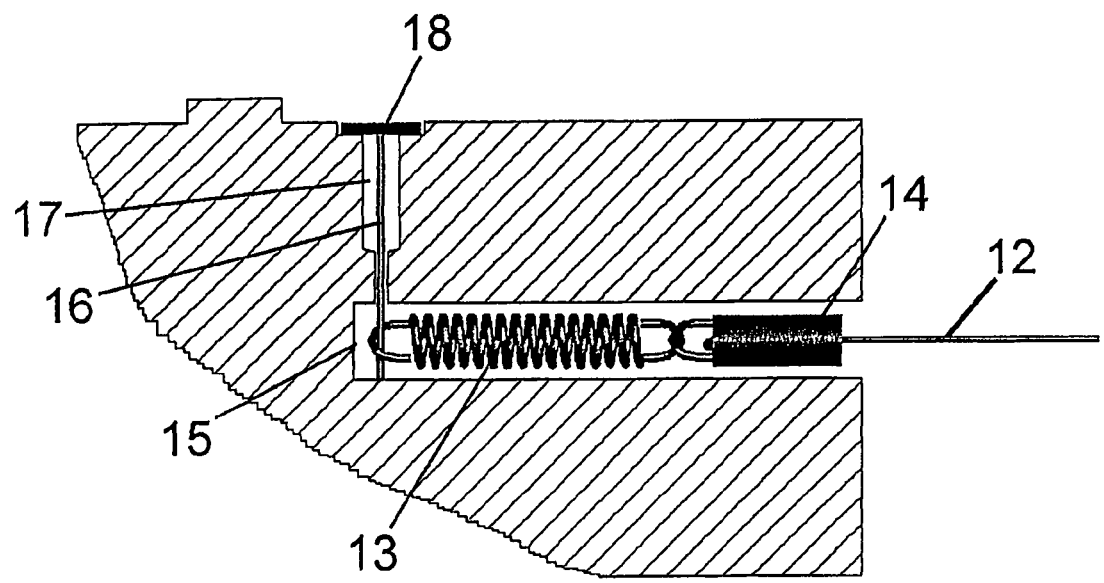
FIG. 5 depicts a detail of the spring suspension with tensile spring.

FIG. 5 depicts the spring suspension used in this example. The suspension, comprising the tensile spring (13) and the ceramic insulating bead (14), is guided into a blind hole (15) and fixed in the rear area using a retention pin (16). The blind hole (15) is located precisely in the direction of elongation of the wire (12) to be placed under tension, and the bore for the pin (17) runs perpendicular to this blind hole (15). The pin is secured against auto-removal during operation by means of the cover (18).

In its axial direction, the insulating bead (14) used has 6 holes that are used to attach a mount for the tensile spring and also through which the measuring wire is threaded.

The arrangement of the tensile spring does not have a negative impact on the seal for the sensor body because the suspension is located entirely within the pressure-conducting area of the sensor and the conduit and there is no contact with the environment, which would have to be sealed. On the side opposing the spring, the electrode wire is conducted in a high-quality steel cannula that is surrounded by a ceramic tube for insulation, the tube being in a channel inside the sensor body. The ceramic tube terminates in a cavity in which the pressure-resistant seal is added by filling with an epoxy resin that can withstand temperatures up to 180° C. The cannula and the electrode wire project out of the sensor body and are sealingly joined at the end using hard soldering. This means that no measuring medium can travel via the gap between cannula and electrode wire to the outside. In the ends of the electrode wires, the latter are connected to the signal lines for connecting to the signals acquisition electronics.

Figure 7:
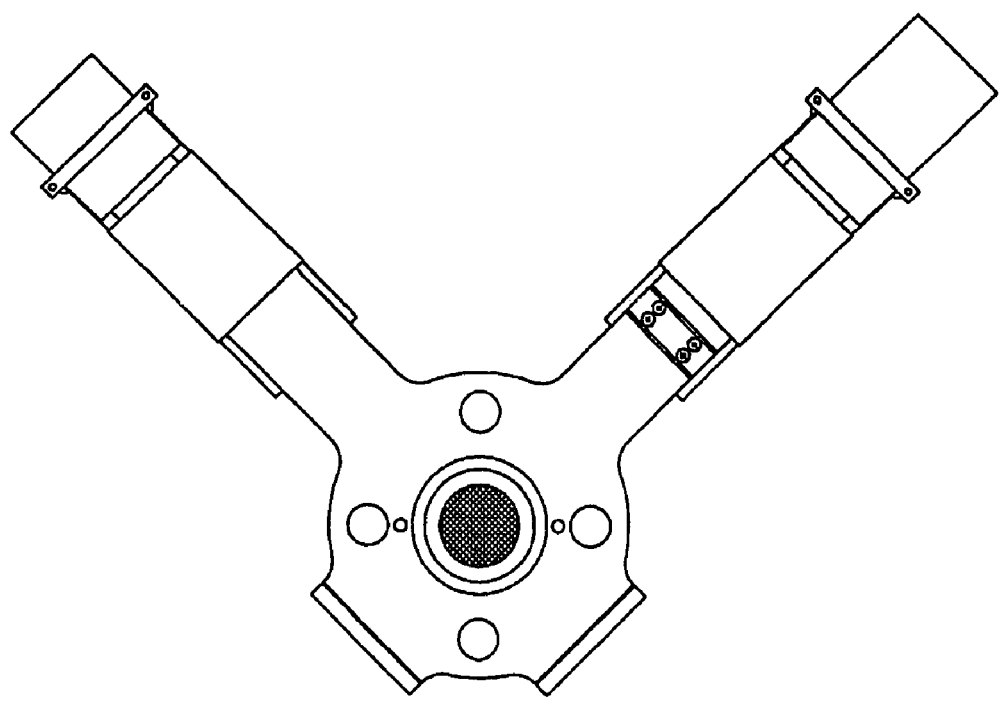

FIG. 7 depicts the second exemplary embodiment. The difference from the first exemplary embodiment is the use of a compression spring rather than a tensile spring.

Figure 6:
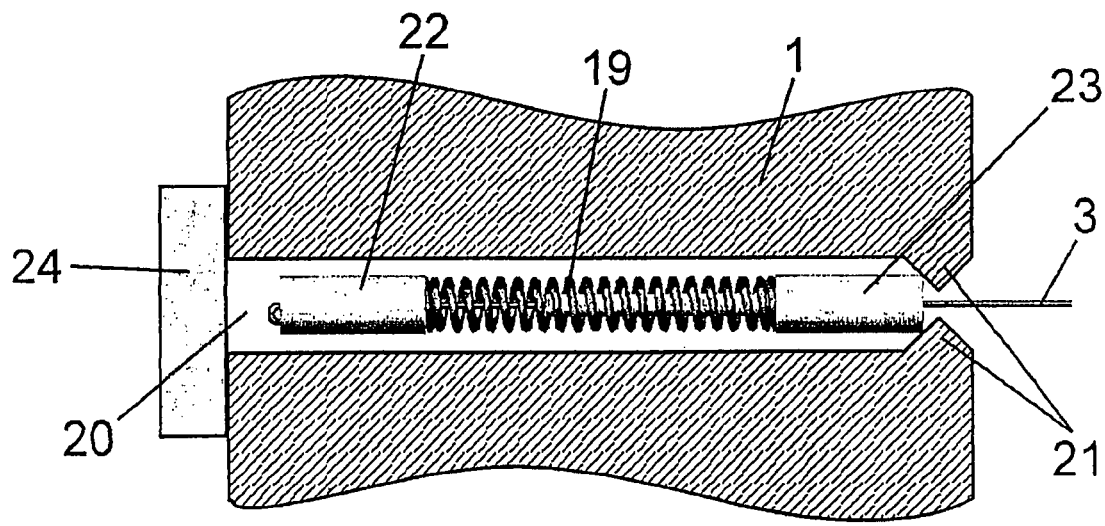
FIG. 6 depicts the use of a compression spring; and,
FIG. 7 depicts the grid sensor with compression spring in its mount.

FIG. 6 depicts how the suspension must be configured in order to use a compression spring. The suspension is added to a channel (20) in the sensor body (1) from the outside, and the electrode wire (3) is conducted through the measuring plane. The suspension is retained in the channel (20) by a sectional constriction (21). Each individual measuring electrode (3) is suspended in an insulating ceramic element (22) and then pulled and placed under tension by a compression spring (19). Care should be taken that the wire (3) cannot touch the compression spring (19). Therefore another insulating ceramic element (23) is added that, during transverse movement by the spring (19), prevents the possibility of electrical contact between the wire (3) and the spring. In contrast to the embodiment of the sensors with tensile springs, in this type of suspension the suspending side must be sealed. This is accomplished with a sealing plate (24) on the exterior contour of the sensor. Each wire grid sensor constructed in this manner has 16 electrode wires per wire grid plane and, like the sensor in the first exemplary embodiment, is suitable for measurements in water/steam flows up to 70 bar and 286° C.

The invention claimed is:

1. A grid sensor for measuring impedance distribution of a fluid in a measuring cross-section of a flow channel, comprising:
    a sensor body including a conduit wall forming an inner boundary of a measuring flow conduit,
    first and second grids of electrode wires that are insulated from one another and from the conduit wall of the measuring flow conduit, said electrode wires being attached in an electrically insulated manner to said sensor body such that each of said electrode wires span the a cross-section of the measuring flow conduit along a span direction, first ones of said electrode wires of said first grid intersecting, without touching, second ones of said electrode wires of said second grid at a pre-specified distance, and each of said electrode wires being individually electrically connectable from outside said sensor body;
    a spring being disposed in a hole in said sensor body, each of said electrode wires being mechanically connected via an insulating bead to said spring, an axis of the hole being in the span direction of a corresponding one of said electrode wires, and the spring being attached to said sensor body in the hole;
    each of said electrode wires being covered, on a side opposing said spring, with an insulating tube that is disposed in a channel in said sensor body that leads outward therefrom,
    said insulating tube terminating in a cavity inside said channel which is filled with a sealing mass,
    neither said insulating bead nor the insulating tube being disposed in the measuring cross-section.

2. A grid sensor in accordance with claim 1, wherein:
    said hole in said sensor body in which said spring is disposed is a blind hole that extends from inside the measuring flow conduit in the span direction of a corresponding one of said electrode wires into said sensor body; and
    said spring is a tensile spring which does not have any connection to outside of said sensor body.

3. A grid sensor in accordance with claim 2, wherein said tensile spring is detachably attached to a pin or a screw that is inserted into a bore perpendicular to the span direction of said corresponding one of said electrode wires that terminates in said blind hole for receiving said tensile spring.

4. A grid sensor in accordance with claim 3, wherein said pin detachably attaches said tensile spring and said tensile spring is fixed in position by a pressure ring.

5. A grid sensor in accordance with claim 1, wherein:
    said hole in said sensor body in which said spring is disposed is a through-bore in said sensor body; and
    said spring is a compression spring that is disposed in the through-bore, and which is positioned in the span direction of a corresponding one of said electrode wires against an edge formed by a sectional constriction of said through-bore such that said corresponding one of said electrode wires is attached to a side of said compression spring that opposes said edge.

6. A grid sensor in accordance with claim 1, wherein each of said electrode wires is covered within said insulating tube, on a side of said sensor body opposing said spring, with a metal cannula to which said wire is sealingly and securely connected outside of said sensor body.

7. A method of measuring impedance distribution of a fluid in a measuring cross-section of a flow channel comprising disposing the grid sensor according to any one of claims 1 to 3 or 4 to 6 in said flow channel.

* * * * *